United States Patent [19]
Knight et al.

[11] Patent Number: 5,811,114
[45] Date of Patent: Sep. 22, 1998

[54] STABILIZED HINOKITIOL AND COMPOSITIONS CONTAINING SAME

[75] Inventors: Althea Knight, Teaneck; Julius Zecchino, Closter, both of N.J.; Steven Schnittger, Huntington Station, N.Y.

[73] Assignee: E-L Management Corp., New York, N.Y.

[21] Appl. No.: 662,870

[22] Filed: Jun. 12, 1996

[51] Int. Cl.⁶ ............................... A01N 25/28; A61K 9/50
[52] U.S. Cl. .......................... 424/408; 424/406; 424/418; 424/401; 424/59; 424/69; 424/499; 424/450; 424/548; 514/675; 514/690
[58] Field of Search ...................... 424/408, 406, 424/499, 59, 69, 401, 418, 548, 195.1, 400; 514/962, 963, 557, 559, 690, 719, 675; 427/213.35; 428/402.2, 402.24; 264/4.1, 4.7; 530/356; 536/54, 55.2

[56] References Cited

U.S. PATENT DOCUMENTS

| | | |
|---|---|---|
| 5,268,174 | 12/1993 | Sakuma . |
| 5,395,620 | 3/1995 | Huc . |
| 5,468,474 | 11/1995 | Honda et al. ........................... 424/70.1 |

FOREIGN PATENT DOCUMENTS

| | | |
|---|---|---|
| 0 471 584 A1 | 2/1992 | European Pat. Off. . |
| 42 02 964 A1 | 8/1993 | Germany . |
| 78035145 | 9/1978 | Japan . |
| 59-085279 | 5/1984 | Japan . |
| 1038203 | 2/1989 | Japan . |
| 2243607 | 9/1990 | Japan . |
| 3133334 | 6/1991 | Japan . |
| 5-86396 | 4/1993 | Japan . |
| 5105898 | 4/1993 | Japan . |
| 5344861 | 12/1993 | Japan . |
| 6090661 | 4/1994 | Japan . |
| 6153788 | 6/1994 | Japan . |
| 6277019 | 10/1994 | Japan . |
| WO 92/05240 | 4/1992 | WIPO . |
| WO 9317559 | 9/1993 | WIPO . |

*Primary Examiner*—Neil S. Levy
*Attorney, Agent, or Firm*—Karen A. Lowney, Esq.

[57] ABSTRACT

The present invention relates to cosmetic or pharmaceutical compositions containing a preservative-effective amount of hinokitiol-containing microcapsules, the microcapsules comprising a matrix containing collagen and a glycosaminoglycan.

14 Claims, No Drawings

STABILIZED HINOKITIOL AND COMPOSITIONS CONTAINING SAME

FIELD OF THE INVENTION

The present invention relates to preservatives useful in pharmaceutical and cosmetic compositions. In particular, the invention relates to a stabilized, anti-irritant preservative, hinokitiol.

BACKGROUND OF THE INVENTION

Contamination of pharmaceutical and cosmetic compositions by bacteria and/or fungi can present a serious problem to the formulator. To combat this problem, and in order to prolong shelf life of the product, such compositions frequently contain preservatives which have antimicrobial activity. Given the diverse chemical nature of the available preservatives, however, and the equally diverse nature of the compositions in which they are intended to be used, the ability to successfully use a given preservative in a particular formulation cannot be assumed.

One such preservative is the substance known as hinokitiol. [2-hydroxy-4-(1-methylethyl)-2,4,6-cycloheptatrien-1-one; isopropyltropolone]. Hinokitiol is a wood extract obtainable from pine, cedar, etc. Methods for its production are described, for example, in JP 0586396 and JP 05105898. This material is known to have potent antimicrobial effects, and, as such, has been previously used for a variety of purposes. For example, hinokitiol has been used in food preservation and prevention of discoloration (JP 78035145; JP 6277019; JP 6153788; JP 6090661; JP 5344861; JP 59085279); in combination with zinc, or with ethyl alcohol and propylene glycol for antisepsis and/or the treatment of infection(WO 9317559; JP 3133334); in detergent compositions (WO 9205240); and as a wood preservative(JP 1038203). Hinokitiol has also been used in various types of cosmetic and pharmaceutical compositions. For example, DE 4202964 discloses a water-phase hair and body treatment comprising hinokitiol and heliotropin or a cosmetic alcohol, wherein the heliotropin and alcohol is said to synergistically enhance the antimicrobial activity of hinokitiol. Similarly, JP 2243607 describes the use in cosmetic compositions of a preservative containing hinokitiol in combination with phenoxyethanol and phthalate ester. In addition, as shown herein, hinokitiol also possesses a heretofore unappreciated anti-irritancy effect.

Although hinokitiol has been shown to be an effective preservative under a wide variety of conditions, it is not itself completely stable under all conditions in which its use might be desired. For example, its use in compositions in polyethylene plastic containers can result in a discolored and/or unpleasant-smelling product. It also may not be stable after direct contact with light or air. These are limitations which under ordinary circumstances would not be acceptable, and which would recommend against its use in a cosmetic composition, where appearance and fragrance can be critical. Therefore, in order to fully exploit its useful properties as a preservative, there remains a need for a means by which hinokitiol can itself be stabilized in the desired composition, and yet retain its useful biological properties, such as antimicrobial and anti-irritant activity. The present invention provides the means by which hinokitiol can be effectively used in cosmetic compositions.

SUMMARY OF THE INVENTION

The present invention provides cosmetic and pharmaceutical compositions containing hinokitiol-containing microcapsules, the microcapsules comprising a matrix containing collagen and a glycosaminoglycan. The microcapsule provides adequate stability to the hinokitiol, preventing it from discoloration and unpleasant odor in the composition containing same, while nonetheless permitting the hinokitiol to exert its preservative and anti-irritant effect on the composition containing it. The invention also provides a method for preserving a cosmetic or pharmaceutical composition, comprising adding to the composition a preservative-effective amount of the hinokitiol containing microcapsules, as well as a method for reducing irritation on the skin by application of a cosmetic composition containing an effective amount of hinokitiol-containing microspheres.

DETAILED DESCRIPTION OF THE INVENTION

The microcapsules used in the present invention are prepared according to the methodology disclosed in U.S. Pat. No. 5,395,620, the contents of which are incorporated herein by reference. Briefly, the microcapsules are prepared by combining a solution containing atelocollagen and a solution containing a polyholoside, preferably a glycosaminoglycan, in the presence of the hinokitiol and a crosslinking agent. Atelocollagen is a type of collagen from which the telopeptides which crosslink typical collagen have been removed. The glycosaminoglycans are well known in the art, and for the present purposes may be selected, for example, from chondroitin 4-sulfate, chondroitin 6-sulfate, dermatan sulfate, heparan sulfate, keratan sulfate, heparin and derivatives thereof; preferably the cosmetically or pharmaceutically acceptable salts, such as calcium or sodium salts, are employed. The amount of glycosaminoglycan present in the microcapsules will typically be about 15–50% by weight of the atelocollagen used in the formulation. In absolute terms, the amount of atelocollagen in the starting solution is approximately 0.5–2% by weight, and the glycosaminoglycan solution contains about 0.5–4%, preferably 0.5–2% by weight of glycosaminoglycans. In a particularly preferred embodiment, both the atelocollagen and the glycosaminoglycans are of marine origin. Cross-linking reagents useful in preparing the microcapsules include, but are not limited to, an acid dichloride, an acid anhydride, or a dibasic or polybasic carboxylic acid. With respect to the hinokitiol, this material is present in an amount of between 0.01–10% by weight, preferably 0.5–4% by weight, of the starting solution.

The microcapsules containing hinokitiol provide an unexpectedly high level of preservative efficacy, while itself remaining stable in the compositions in which it is included. The retention of antimicrobial activity, at the levels seen herein, is particularly surprising in view of the fact that the hinokitiol itself is not expected to be in direct contact with the medium it is intended to preserve. The microcapsules in which the hinokitiol is contained are essentially impermeable, i.e., there is apparently substantially no leakage of the hinokitiol into the medium in which the microcapsules are contained, as evidenced by the absence of unpleasant odor or color in the products containing them. Since the hinokitiol is used in quantities essentially the same as used in its unencapsulated form, the substantially complete retention of antimicrobial activity by the "protected" hinokitiol is quite unexpected.

The encapsulated hinokitiol can be used in a wide variety of cosmetic and/or pharmaceutical compositions, as well as a preservative in food compositions. In particular, the hinokitiol can be used in virtually any form in which such compositions may be formulated, e.g., solutions, colloidal dispersions, emulsions, suspensions, creams, lotions, gels, foams, mousses and the like. Methods and components for preparing such compositions are well known in the art, and can be found for example, in CTFA International Cosmetics Ingredients Dictionary, The Cosmetic, Toiletry, and Fragrance Association, Washington, DC, 1991. The amount of the hinokitiol-containing microspheres will vary depending on the nature of the composition and the amount of hinokitiol contained in the microspheres, but a preservative-effective amount of hinokitiol per se will generally be in the range of from about 0.1–1% by weight of the composition as a whole, given the amount of hinokitiol in the microspheres is as stated above. It is well within the skill of the art to determine the desired microsphere concentration in the formulation, given these parameters.

The compositions of the present invention will also comprise a pharmaceutically or cosmetically acceptable carrier, in an amount appropriate to accomodate the other components of the formulation. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. The carrier may be in any form appropriate to the mode of delivery, for example, solutions, colloidal dispersions, emulsions, suspensions, creams, lotions, gels, foams, mousses and the like.

In a preferred embodiment, the carrier is a suspension, dispersion or emulsion. The emulsion may be an oil-in-water emulsion, or a water-in-oil emulsion. These emulsions contain one or more oil components, an aqueous component, and a specific emulsifier component chosen depending on the nature of the desired emulsion.

The oil component may be any pharmaceutically or cosmetically acceptable material which is substantially insoluble in water. These materials can be found for example in the CTFA International Dictionary of Cosmetic Ingredients as well as the U.S. Pharmacopoeia or equivalent sources. Suitable oil components include, but are not limited to, natural oils, such as coconut oil; hydrocarbons, such as mineral oil and hydrogenated polyisobutene; fatty alcohols, such as octyldodecanol; esters, such as C12–15 alkyl benzoate; diesters, such as propylene glycol dipelargonate; triesters, such as glyceryl trioctanoate; sterol derivatives, such as lanolin; animal waxes, such as beeswax; plant waxes, such as carnauba; mineral waxes, such as ozokerite; petroleum waxes, such as paraffin wax; synthetic waxes, such as polyethylene; and mixtures thereof. Suitable oil components may also be silicones including, but not limited to, volatile silicones such as cyclomethicone; polymeric silicones such as dimethicone; alkylated derivatives of polymeric silicones, such as cetyl dimethicone and lauryl trimethicone; hydroxylated derivatives of polymeric silicones, such as dimethiconol; and mixtures thereof. The aqueous component refers to any pharmaceutically or cosmetically acceptable material consisting essentially or predominantly of water.

For preparation of an oil-in water emulsion, the oil-in-water emulsifier will be an emulsifier having a hydrophilic-lipophilic balance(HLB) of at least 6, or a mixture of such emulsifiers with one or more water-in-oil emulsifiers(i.e., emulsifiers having an HLB of from about 2 to about 6), in which case the type and amount of each emulsifier present in the mixture is selected such that the effective HLB of the resultant oil-in-water emulsifier component is at least about 6. Techniques for combining and ascertaining the effective HLB of a mixture of emulsifiers are known; see L. M. Prince, in M. G. DeNavarre, "The Chemistry and Manufacture of Cosmetics", Volume III, Second Ed., (Continental Press, Orlando, 1975), pp. 25–37.

Suitable oil-in-water emulsifiers include, but are not limited to, sorbitol derivatives, such as sorbitan monolaurate and polysorbate 20; ethoxylated alcohols such as laureth-23, ethoxylated fatty acids such as PEG-1000 stearate; amidoamine derivatives such as stearamidoethyl diethylamine; sulfate esters such as sodium lauryl sulfate; phosphate esters such as DEA cetyl phosphate; fatty acid amine salts such as TEA stearate; and mixtures thereof.

The emulsion may also be a water-in-oil emulsion. For this purpose, a water-in-oil emulsifier is employed. This refers to any cosmetically acceptable emulsifier having an HLB of no greater than 6, preferably from about 2 to about 4. Suitable water-in-oil emulsifiers include, but are not limited to, sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2 lactylate; lecithin; and mixtures thereof The active component of the pharmaceutical or cosmetic compositions will depend on the intended purpose of the compositions. Examples of such active agents which may form part of the composition include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, antiinflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, vitamins, corticosteroids, tanning agents, hormones, retinoids, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinoic acid, 13-cis retinoic acid, hydrocortisone, hydrocortisone 21-acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, vitamin A palmitate, vitamin E acetate and mixtures thereof.

In one preferred embodiment, the composition is a sunscreen-containing composition. The term "sunscreen" as used herein refers to any material which is capable of protecting human skin from ultraviolet radiation having a wavelength of from about 280 to about 400nm, by effectively absorbing such radiation, and/or reflecting or scattering such radiation away from the surface of human skin. Suitable sunscreens for purposes of this invention include but not limited to, titanium derivatives such as titanium dioxide, especially titanium dioxide having an average particle size of from 10 to 100 nanometers, most especially titanium dioxide having an average particle size of from 10 to 100 nanometers and comprising a hydrophobic coating agent to minimize agglomeration; zinc derivatives such as zinc oxide, especially zinc oxide having an average particle size of from 10 to 100 nanometers; melanin and melanin derivatives; dioxybenzone; 2-ethylhexyl 2-cyano-3,3-diphenylacrylate; 2-ethylhexyl p-methoxycinnamate; 2-ethylhexyl salicylate; homosalate; menthyl anthranilate; oxybenzone; octyl dimethyl PABA; red petrolatum; ferulic acid ester; and mixtures thereof.

In addition to those components specifically noted above, the compositions may also comprise additional preservatives, fragrances, emollients, antiseptics, antiinflammatories, antibacterials, stabilizers, antioxidants, vitamins, pigments, dyes, humectants, and propellants, as well as other classes of materials the presence of which in the compositions may be cosmetically, medicinally, or otherwise desired. Such components can be found in the CTFA International Cosmetics Ingredients Dictionary, supra.

The present invention is further illustrated by the following non-limiting examples.

EXAMPLE 1

Thalaspheres® (30μm) containing hinokitiol are provided by Bioetica, Inc., Portland, Maine). The composition of the Thalaspheres®, in grams per 100g, is as follows:

| Ingredient | Total | Support phase | Capsules composition |
|---|---|---|---|
| Deionized water | 81.494 | 77.86% | 89.98% |
| Butylene glycol | 15.0 | 21.43% | |
| Hinokitiol | 2.4 | | 8.0% |
| Xanthan gum | 0.5 | 0.71% | |
| atelocollagen | 0.441 | | 1.47% |
| chondroitin | 0.165 | | 0.55% |
| | 100 g | 100% | 100% |
| equivalent(in g/100 g of product) | | 70 g | 30 g |

EXAMPLE 2

The encapsulated hinokitiol, as described in Example 1, is incorporated by art-recognized procedures into a sunscreen-containing dispersion, a moisturizing cream emulsion, and a skin desensitizing lotion emulsion. The components are as follows:

| Component | Weight % |
|---|---|
| SUNSCREEN FORMULATION | |
| cyclomethicone/dimethicone copolyol | 16.0 |
| Titanium dioxide Dispersion | 13.0 |
| cyclomethicone | 15.5 |
| dimethicone | 10.5 |
| phenyltrimethicone | 6.0 |
| hydrogenated lecithin | 0.5 |
| deionized water | 36.0 |
| magnesium sulfate | 1.5 |
| encapsulated hinokitiol | 1.0 |
| MOISTURIZING FORMULATION | |
| Deionized water | 62.0 |
| oat stearate | 0.9 |
| Disodium EDTA | 0.1 |
| squalane | 5.0 |
| cetearyl alcohol/cetearyl glucoside | 5.0 |
| shea butter | 6.0 |
| sucrose | 2.0 |
| isostearyl neopentanoate | 2.0 |
| cyclomethicone | 7.5 |

-continued

| Component | Weight % |
|---|---|
| carbomer | 0.25 |
| glycerine USP 95% | 2.5 |
| triethanolamine 99% | 0.05 |
| sodium hyaluronate | 2.5 |
| encapsulated hinokitiol | 4.2 |
| SKIN DESENSITIZING FORMULATION | |
| Satin Finish* | 50% |
| Disodium EDTA | 0.1 |
| Shea butter | 0.5 |
| rosemary extract | 0.1 |
| glycerine USP 95% | 4.5 |
| gorgonian extract | 0.1 |
| aluminum starch octenyl succinate | 1.2 |
| carbomer | 0.2 |
| sucrose | 1.8 |
| caffeine powder | 0.4 |
| triethanolamine 99% | 0.05 |
| magnesium aluminum sulfate | 0.25 |
| deionized water | 36.6 |
| encapsulated hinokitiol | 4.2 |

*a commercial(Collaborative Labs) emulsion comprising phenyl trimethicone, cyclomethicone, phosophoglycerides, dimethiconol, phenoxyethanol, carbomer, and triethanolamine The formulations so prepared exhibit no deterioration, no discoloration and no unpleasant odor even after prolonged storage, showing the encapsulated hinokitiol retains its preservative effect while at the same time being stabilized by the encapsulation.

EXAMPLE 3

Hinokitiol alone is tested for its ability to prevent irritation. Hinokitiol (unencapsulated, 0.5% by weight)is applied to the ventral forearms of panelists. The material is allowed to absorb for twenty minutes and then Balsam of Peru, an irritant, is applied to the test sites. Skin irritation is measured in terms of increase in skin redness. Cola nitida(10% hydro-alcohol 1:1) is used as a positive control.

The degree of redness is measured with the Minolta chromameter and compared with the positive and negative controls. The positive control is the color of skin treated with Balsam of Peru alone and the negative control is the skin treated with cola material challenged as with the hinokitiol. Hinokitiol exhibits a 71% activity, as compared with an average of 67% for cola.

The encapsulated hinokitiol is then tested for its retained anti-irritant activity. Encapsulated hinokitiol, prepared as described above, is prepared in 4.2% and 2.8% aqueous solution. These solutions are tested against empty microcapsules, as well as against cola nitida(10% hydro-alcohol 1:1), using the same protocol as described in the previous example. Results show that the activity of the encapsulated hinokitiol at 4.2% is approximately equivalent to that of 10% cola (61% vs 64%, respectively) in reducing the onset of irritation due to Balsam of Peru. The lower concentration of hinokitiol capsules shows 53% activity, while empty microcapsules show 28% activity.

What we claim is:

1. A cosmetic or pharmaceutical composition containing a preservative-effective amount of hinokitiol-containing microcapsules, the microcapsules comprising a matrix containing collagen and a glycosaminoglycan.

2. The composition of claim 1, in which the matrix comprises atelocollagen and chondroitin sulfate.

3. The composition of claim 1 in which the hinokitiol is present in the microcapsules in an amount of from 0.1–10% by weight.

4. The composition of claim 1 in which the microcapsules are present in an amount of from about 1–10%.

5. The composition of claim 1 which is in the form of a solution, colloidal dispersion, emulsion, suspension, cream, lotion, gel, foam, or mousse.

6. The composition of claim 5 which is a dispersion.

7. The composition of claim 5 which is an emulsion.

8. The composition of claim 7 which is a water-in-oil emulsion.

9. The composition of claim 6 which also contains a sunscreen.

10. The composition of claim 9 in which the sunscreen is titanium dioxide.

11. The composition of claim 10 in which the microcapsules are present in an amount of about 1–5%.

12. A food composition containing a preservative-effective amount of hinokitiol-containing microcapsules, the microcapsules comprising a matrix containing collagen and a glycosaminoglycan.

13. A method for preserving a pharmaceutical, food or cosmetic composition comprising adding to the composition a preservative effective amount of hinokitiol-containing microcapsules.

14. A method for reducing the irritating effects of a cosmetic or pharmaceutical composition on the skin comprising adding to the composition an anti-irritant effective amount of hinokitiol-containing microcapsules.

\* \* \* \* \*